United States Patent
Orszulak

(10) Patent No.: US 10,993,761 B2
(45) Date of Patent: *May 4, 2021

(54) ELECTROSURGICAL APPARATUS WITH REAL-TIME RF TISSUE ENERGY CONTROL

(71) Applicant: COVIDIEN LP, Mansfield, MA (US)

(72) Inventor: James H. Orszulak, Nederland, CO (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/559,295

(22) Filed: Sep. 3, 2019

(65) Prior Publication Data

US 2019/0388138 A1 Dec. 26, 2019

Related U.S. Application Data

(63) Continuation of application No. 14/692,195, filed on Apr. 21, 2015, now Pat. No. 10,413,347, which is a (Continued)

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1233* (2013.01); *A61B 18/1445* (2013.01);
(Continued)

(58) Field of Classification Search
CPC ............ A61B 18/1206; A61B 18/1233; A61B 2018/128; A61B 2018/00636–00904;
(Continued)

(56) References Cited

U.S. PATENT DOCUMENTS 3,757,241 A 9/1973 Kime
3,826,263 A 7/1974 Cage et al.
(Continued)

FOREIGN PATENT DOCUMENTS

DE 179607 C 11/1906
DE 390937 C 3/1924
(Continued)

OTHER PUBLICATIONS

Cosman et al., "Theoretical Aspects of Radiofrequency Lesions in the Dorsal Root Entry Zone" Neurosurgery 15: (1984) pp. 945-950.
(Continued)

*Primary Examiner* — Jaymi E Della
*Assistant Examiner* — Sean W Collins
(74) *Attorney, Agent, or Firm* — Carter, DeLuca & Farrell LLP

(57) ABSTRACT

A radio-frequency (RF) amplifier having a direct response to an arbitrary signal source to output one or more electrosurgical waveforms within an energy activation request, is disclosed. The RF amplifier includes a phase compensator coupled to an RF arbitrary source, the phase compensator configured to generate a reference signal as a function of an arbitrary RF signal from the RF arbitrary source and a phase control signal; at least one error correction amplifier coupled to the phase compensator, the at least one error correction amplifier configured to output a control signal at least as a function of the reference signal; and at least one power component coupled to the at least one error correction amplifier and to a high voltage power source configured to supply high voltage direct current thereto, the at least one power component configured to operate in response to the control signal to generate at least one component of the at least one electrosurgical waveform.

13 Claims, 4 Drawing Sheets

Related U.S. Application Data continuation of application No. 13/195,607, filed on Aug. 1, 2011, now Pat. No. 9,028,479.

(51) Int. Cl.
  *H03F 3/24* (2006.01)
  *H03F 1/30* (2006.01)
  *A61B 18/18* (2006.01)
  *A61B 18/00* (2006.01)

(52) U.S. Cl.
  CPC ....... *A61B 18/1402* (2013.01); *A61B 18/1815* (2013.01); *A61B 2018/00607* (2013.01); *A61B 2018/00702* (2013.01); *A61B 2018/00726* (2013.01); *A61B 2018/00732* (2013.01); *A61B 2018/00761* (2013.01); *A61B 2018/00767* (2013.01); *A61B 2018/00827* (2013.01); *A61B 2018/00845* (2013.01); *A61B 2018/00869* (2013.01); *A61B 2018/128* (2013.01); *H03F 1/30* (2013.01); *H03F 3/24* (2013.01); *H03F 2200/153* (2013.01); *H03F 2203/45138* (2013.01); *H03F 2203/45456* (2013.01); *H03F 2203/45731* (2013.01)

(58) Field of Classification Search
  CPC ....... A61B 2018/1823; H03F 2200/153; H03F 2203/45138
  See application file for complete search history.

(56) References Cited

U.S. PATENT DOCUMENTS

| | | |
|---|---|---|
| 3,978,393 A | 8/1976 | Wisner et al. |
| 4,247,815 A | 1/1981 | Larsen et al. |
| 4,658,819 A | 4/1987 | Harris et al. |
| 4,818,954 A | 4/1989 | Flachenecker et al. |
| 5,024,668 A | 6/1991 | Peters et al. |
| 5,113,116 A | 5/1992 | Wilson |
| 5,325,073 A | 6/1994 | Hasegawa |
| 5,341,807 A | 8/1994 | Nardella |
| 5,438,302 A | 8/1995 | Goble |
| 5,531,774 A | 7/1996 | Schulman et al. |
| 5,559,688 A | 9/1996 | Pringle |
| 5,628,771 A | 5/1997 | Mizukawa et al. |
| 6,017,354 A | 1/2000 | Culp et al. |
| 6,090,123 A | 7/2000 | Culp et al. |
| 6,188,211 B1 | 2/2001 | Rincon-Mora et al. |
| 6,329,778 B1 | 12/2001 | Culp et al. |
| 6,477,426 B1 | 11/2002 | Fenn et al. |
| 6,740,079 B1 | 5/2004 | Eggers et al. |
| 6,923,804 B2 | 8/2005 | Eggers et al. |
| 6,966,907 B2 | 11/2005 | Goble |
| 7,058,372 B1 | 6/2006 | Pardoen et al. |
| 7,190,933 B2 | 3/2007 | De Ruijter et al. |
| D574,323 S | 8/2008 | Waaler |
| 7,422,582 B2 | 9/2008 | Malackowski et al. |
| 7,517,351 B2 | 4/2009 | Culp et al. |
| 7,525,398 B2 | 4/2009 | Nishimura et al. |
| 7,927,328 B2 | 4/2011 | Orszulak et al. |
| 9,028,479 B2 | 5/2015 | Orszulak |
| 2003/0181898 A1 | 9/2003 | Bowers |
| 2007/0129716 A1 | 6/2007 | Daw et al. |
| 2007/0173806 A1 | 7/2007 | Orszulak et al. |
| 2009/0248003 A1 | 10/2009 | Orszulak |
| 2010/0063494 A1 | 3/2010 | Orszulak |
| 2010/0324549 A1 | 12/2010 | Marion |
| 2011/0087213 A1 | 4/2011 | Messerly et al. |
| 2011/0087256 A1 | 4/2011 | Wiener et al. |
| 2011/0115562 A1 | 5/2011 | Gilbert |
| 2011/0178516 A1 | 7/2011 | Orszulak et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 0325456 A2 | 7/1989 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| EP | 0246350 A1 | 11/1987 |
| EP | 0267403 A2 | 5/1988 |
| EP | 0296777 A2 | 12/1988 |
| EP | 0310431 A2 | 4/1989 |
| EP | 0336742 A2 | 10/1989 |
| EP | 0390937 A1 | 10/1990 |
| EP | 0556705 A1 | 8/1993 |
| EP | 0608609 A2 | 8/1994 |
| EP | 0836868 A2 | 4/1998 |
| EP | 0880220 A2 | 11/1998 |
| EP | 0882955 A1 | 12/1998 |
| EP | 1051948 A2 | 11/2000 |
| EP | 1366724 A1 | 12/2003 |
| EP | 1681026 A2 | 7/2006 |
| EP | 1776929 A1 | 4/2007 |
| EP | 1810632 A1 | 7/2007 |
| EP | 2025297 A2 | 2/2009 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |
| JP | 2008279254 A | 11/2008 |
| JP | 2009240780 A | 10/2009 |
| JP | 2011109663 A | 6/2011 |
| SU | 166452 | 11/1964 |
| SU | 727201 A2 | 4/1980 |
| WO | 0211634 A1 | 2/2002 |
| WO | 0245589 A2 | 6/2002 |
| WO | 03090635 A1 | 11/2003 |
| WO | 2004/078050 A2 | 9/2004 |
| WO | 2006050888 A1 | 5/2006 |
| WO | 2007067522 A2 | 6/2007 |
| WO | 2008043999 A2 | 4/2008 |
| WO | 2008053532 A1 | 5/2008 |

OTHER PUBLICATIONS

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300" 1 p. Sep. 1998.

Valleylab Brochure "Valleylab Electroshield Monitoring System" 2 pp. Nov. 1995.

International Search Report EP 98300964.8 dated Dec. 4, 2000.

International Search Report EP 04009964 dated Jul. 13, 2004.

(56) References Cited

OTHER PUBLICATIONS

International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report and Written Opinion from corresponding application PCT/US2012/048782 dated Jan. 17, 2013.
U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/793,136, filed Jun. 3, 2010, Gary M. Couture.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 12, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
U.S. Appl. No. 13/034,822, filed Feb. 25, 2011, Mark A. Johnston.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/227,704, filed Sep. 8, 2011, Thomas Plaven.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/246,035, filed Sep. 27, 2011, Darren Odom.
U.S. Appl. No. 13/247,043, filed Sep. 28, 2011, Donald W. Heckel.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (Jun. 1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. Feb. 2005.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At Vhf Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51:(1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B. V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.

(56) References Cited

OTHER PUBLICATIONS

Vallfors et al., "Automatically Controlled Bipolar Electrosoagulation—'COA-COMP'", Neurosurgical Review 7:2-3 (1984) pp. 187-190.
Prutchi et al. "Design and Development of Medical Electronic Instrumentation", John Wiley & Sons, Inc. 2005.
Chinese Office Action from Appl. No. 201280031800.9 dated Nov. 2, 2015.
Canadian Office Action dated Mar. 5, 2018 issued in corresponding Canadian Appln. No. 2,843,393.
Canadian Office Action dated Dec. 19, 2018 issued in corresponding CA Appln. No. 2,843,393.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11155959.7 dated Jun. 30, 2011.
International Search Report EP11155960.5 dated Jun. 10, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
Australian Examination Report from Appl. No. AU 2012290253 dated Apr. 13, 2016.
Japanese Office Action from Appl. No. 2014-524005 dated May 25, 2016.

ELECTROSURGICAL APPARATUS WITH REAL-TIME RF TISSUE ENERGY CONTROL

CROSS-REFERENCE TO RELATED APPLICATIONS

This application is a continuation application of U.S. patent application Ser. No. 14/692,195, filed Apr. 21, 2015, which is a continuation of U.S. patent application Ser. No. 13/195,607, filed on Aug. 1, 2011, now U.S. Pat. No. 9,028,479. The entire contents of all of the foregoing applications are incorporated by reference herein.

BACKGROUND

Technical Field

The present disclosure relates to electrosurgical apparatuses, systems and methods. More particularly, the present disclosure is directed to an electrosurgical generator adapted for real-time adjustment of its output.

Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current, microwave energy or resistive heating to a surgical site to cut, ablate, coagulate or seal tissue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes.

Bipolar electrosurgical techniques and instruments can be used to coagulate blood vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. In order to achieve one of these desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

In monopolar electrosurgery, the active electrode is typically a part of the surgical instrument held by the surgeon that is applied to the tissue to be treated. A patient return electrode is placed remotely from the active electrode to carry the current back to the generator and safely disperse current applied by the active electrode. The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

Conventional electrosurgical generators operate in one operational mode (e.g., cutting, coagulation, spray, etc.) which is set prior to commencement of the procedure during a given activation period. If during treatment a need arises to switch form one mode to another, such as during a cutting procedure when a vessel is cut and begins to bleed, the first mode (e.g., cutting) is terminated manually and the second mode (e.g., coagulation) is switched on. There is a need for an electrosurgical generator which can switch between a plurality of modes automatically in response to sensed tissue and/or energy feedback signals.

SUMMARY

A radio-frequency (RF) amplifier for outputting at least one electrosurgical waveform is disclosed. The RF amplifier includes a phase compensator coupled to an RF arbitrary source, the phase compensator configured to generate a reference signal as a function of an arbitrary RF signal from the RF arbitrary source and a phase control signal; at least one error correction amplifier coupled to the phase compensator, the at least one error correction amplifier configured to output a control signal at least as a function of the reference signal; and at least one power component coupled to the at least one error correction amplifier and to a high voltage power source configured to supply high voltage direct current thereto, the at least one power component configured to operate in response to the control signal to generate at least one component of the at least one electrosurgical waveform.

In another embodiment, an RF amplifier configured to output at least one electrosurgical waveform in response to an arbitrary RF signal is disclosed. The RF amplifier includes a phase compensator coupled to an RF arbitrary source, the phase compensator configured to generate a reference signal as a function of an arbitrary RF signal from the RF arbitrary source and a phase control signal; at least one error correction amplifier coupled to the phase compensator, the at least one error correction amplifier configured to output a control signal at least as a function of the reference signal; at least one power component coupled to the at least one error correction amplifier, the at least one power component configured to operate in response to the control signal to generate at least one component of the at least one electrosurgical waveform; at least one current sensor configured to measure current of the at least one electrosurgical waveform and to operate with the at least one power component to output a current control signal as a function of the measured current; a patient isolation transformer coupled to the RF amplifier, the patient isolation transformer including a primary winding coupled to the at least one power component, wherein the patient isolation is the only isolation coupling component for delivering the at least one electrosurgical waveform to a patient and is configured to operate in a phase-correlated manner with the at least one electrosurgical waveform of the RF amplifier; and a high voltage power source configured to supply high voltage direct current to the RF amplifier.

In embodiments, an electrosurgical generator is disclosed. The generator includes a high voltage power source configured to supply high voltage direct current; an RF arbitrary source configured to generate an arbitrary RF signal; and a radio-frequency (RF) amplifier configured to output at least one electrosurgical waveform. The RF amplifier includes: a phase compensator coupled to the RF arbitrary source, the phase compensator configured to generate a reference signal as a function of the arbitrary RF signal from the RF arbitrary source and a phase control signal; at least one error correction amplifier coupled to the phase compensator, the at least one error correction amplifier configured to output a control signal at least as a function of the reference signal; and at least one power component coupled to the at least one error correction amplifier and to the high voltage power source, the at least one power component configured to operate in response to the control signal to generate at least one component of the at least one electrosurgical waveform. The generator also includes a controller configured to adjust at least one of the arbitrary RF signal and the phase control signal in response to at least one selected electrosurgical operational mode.

According to another embodiment of the present disclosure, an electrosurgical generator is disclosed. The generator includes a high voltage power source configured to supply high voltage direct current; an RF arbitrary source configured to generate an arbitrary RF signal; and one or more radio-frequency (RF) amplifiers configured to output at least one electrosurgical waveform. The radio-frequency (RF) amplifiers include: a phase compensator coupled to the RF arbitrary source, the phase compensator configured to generate a reference signal as a function of the arbitrary RF signal from the RF arbitrary source and a phase control signal; a first control loop and a second control loop. The first control loop includes a first error correction amplifier coupled to the phase compensator, the first error correction amplifier configured to output a first control signal at least as a function of the reference signal and a first power component coupled to the first error correction amplifier and to the high voltage power source, the first power component configured to operate in response to the first control signal to generate a first component of the at least one electrosurgical waveform. The second control loop includes a second error correction amplifier coupled to the phase compensator, the second error correction amplifier configured to output a second control signal at least as a function of the reference signal; and a second power component coupled to the second error correction amplifier and to the high voltage power source, the second power component configured to operate in response to the second control signal to generate a second component of the at least one electrosurgical waveform. The generator also includes a controller configured to adjust at least one of the arbitrary RF signal and the phase control signal in response to at least one selected electrosurgical operational mode.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The generator according to the present disclosure can perform monopolar and/or bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., ablation, coagulation, cutting, blending, division, etc.) and procedures (e.g., monopolar, bipolar, vessel sealing).

Figure 1:
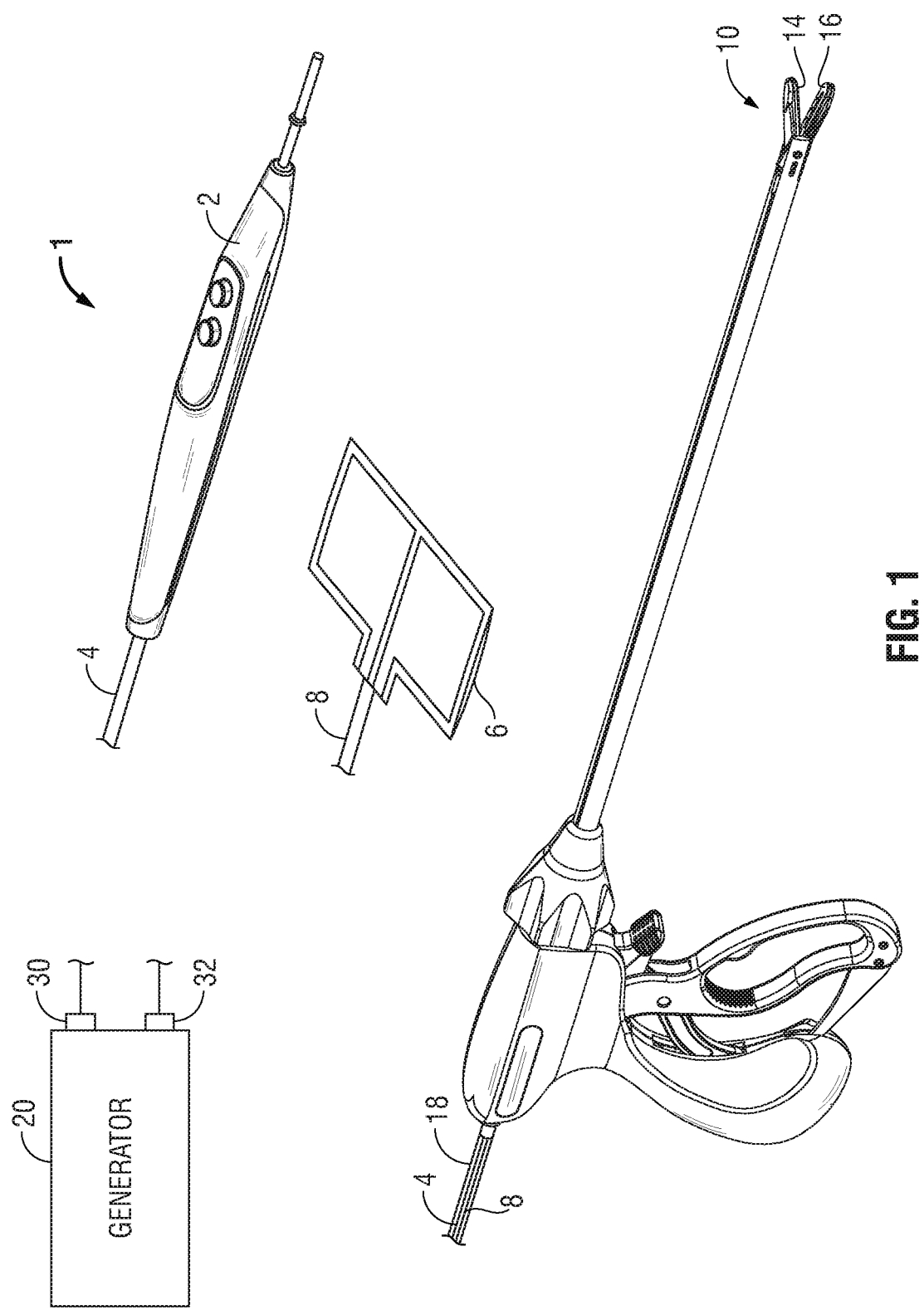
FIG. 1 is a schematic block diagram of an electrosurgical system according to one embodiment of the present disclosure.

FIG. 1 is a schematic illustration of a bipolar and monopolar electrosurgical system 1 according to one embodiment of the present disclosure. The system 1 includes one or more monopolar electrosurgical instruments 2 having one or more electrodes (e.g., electrosurgical cutting probe, ablation electrode(s), etc.) for treating tissue of a patient. Electrosurgical energy is supplied to the instrument 2 by a generator 20 via a supply line 4 that is connected to an active terminal 30 of the generator 20, allowing the instrument 2 to coagulate, ablate and/or otherwise treat tissue. The energy is returned to the generator 20 through a return electrode 6 via a return line 8 at a return terminal 32 of the generator 20. The system 1 may include a plurality of return electrodes 6 that are arranged to minimize the chances of tissue damage by maximizing the overall contact area with the patient. In addition, the generator 20 and the return electrode 6 may be configured for monitoring so-called "tissue-to-patient" contact to insure that sufficient contact exists therebetween to further minimize chances of tissue damage.

The system 1 may also include a bipolar electrosurgical forceps 10 having one or more electrodes for treating tissue of a patient. The electrosurgical forceps 10 includes opposing jaw members having one or more active electrodes 14 and a return electrode 16 disposed therein. The active electrode 14 and the return electrode 16 are connected to the generator 20 through cable 18 that includes the supply and return lines 4, 8 coupled to the active and return terminals 30, 32, respectively. The electrosurgical forceps 10 is coupled to the generator 20 at a connector 60 or 62 (FIG. 2) having connections to the active and return terminals 30 and 32 (e.g., pins) via a plug (not shown) disposed at the end of the cable 18, wherein the plug includes contacts from the supply and return lines 4, 8.

Figure 2:
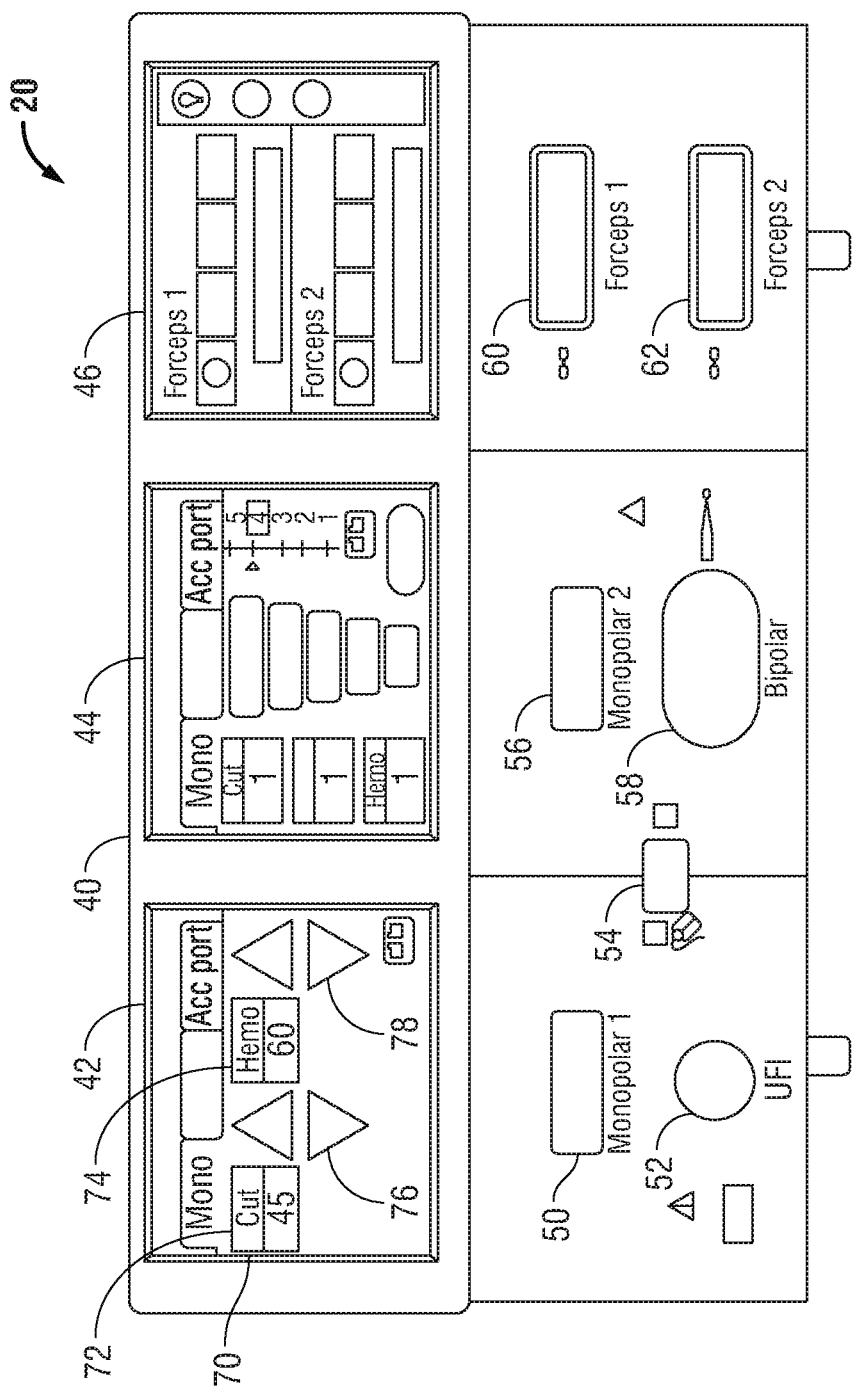
FIG. 2 is a front view of an electrosurgical generator according to an embodiment of the present disclosure.

With reference to FIG. 2, the generator 20 may be any suitable type (e.g., electrosurgical, microwave, etc.) and may include a plurality of connectors 50-62 to accommodate various types of electrosurgical instruments (e.g., multiple instruments 2, electrosurgical forceps 10, etc.). With reference to FIG. 2, front face 40 of the generator 20 is shown. The generator 20 includes one or more display screens 42, 44, 46 for providing the user with variety of output information (e.g., intensity settings, treatment complete indicators, etc.). Each of the screens 42, 44, 46 is associated with a corresponding connector 50-62. The generator 20 includes suitable input controls (e.g., buttons, activators, switches, touch screen, etc.) for controlling the generator 20. The display screens 42, 44, 46 are also configured as touch screens that display a corresponding menu for the electrosurgical instruments (e.g., multiple instruments 2, electrosurgical forceps 10, etc.). The user then makes inputs by simply touching corresponding menu options.

The generator 20 is configured to operate in a variety of modes. In one embodiment, the generator 20 may output the following modes, cut, blend, division with hemostasis, fulgurate and spray. Each of the modes operates based on a preprogrammed power curve that dictates how much power is output by the generator 20 at varying impedance ranges of the load (e.g., tissue). Each of the power curves includes power, voltage and current control range that are defined by the user-selected power setting and the measured minimum impedance of the load.

In the cut mode, the generator 20 may supply a continuous sine wave at a predetermined frequency (e.g., 472 kHz) having a crest factor of about 1.5 with an impedance of from about 100Ω to about 2,000Ω. The cut mode power curve may include three regions: constant current into low impedance, constant power into medium impedance and constant voltage into high impedance. In the blend mode, the generator may supply bursts of a sine wave at the predetermined frequency, with the bursts reoccurring at a first predetermined rate (e.g., about 26.21 kHz). In one embodiment, the duty cycle of the bursts may be about 50%. The crest factor of one period of the sine wave may be about 1.5. The crest factor of the burst may be about 2.7.

The division with hemostasis mode may include bursts of sine waves at a predetermined frequency (e.g., 472 kHz) reoccurring at a second predetermined rate (e.g., about 28.3 kHz). The duty cycle of the bursts may be about 25%. The crest factor of one burst may be about 4.3 across an impedance of from about 100Ω to about 2,000Ω. The fulgurate mode may include bursts of sine waves at a predetermined frequency (e.g., 472 kHz) reoccurring at a third predetermined rate (e.g., about 30.66 kHz). The duty cycle of the bursts may be about 6.5% and the crest factor of one burst cycle may be about 5.55 across an impedance range of from about 100Ω to about 2,000Ω. The spray mode may include bursts of sine wave at a predetermined frequency (e.g., 472 kHz) reoccurring at a fourth predetermined rate (e.g., about 21.7 kHz). The duty cycle of the bursts may be about 4.6% and the crest factor of one burst cycle may be about 6.6 across the impedance range of from about 100Ω to about 2,000Ω.

The screen 46 of FIG. 2 controls bipolar sealing procedures performed by the forceps 10 that may be plugged into the connectors 60 and 62. The generator 20 outputs energy through the connectors 60 and 62 suitable for sealing tissue grasped by the forceps 10. The screens 42 and 44 control monopolar output and the devices connected to the connectors 50 and 56. The connector 50 is configured to couple to the instrument 2 and the connector 52 is configured to couple to a foot switch (not shown). The foot switch provides for additional inputs (e.g., replicating inputs of the generator 20 and/or instrument 2). The screen 44 controls monopolar and bipolar output and the devices connected to the connectors 56 and 58, respectively. Connector 56 is configured to couple to the instrument 2, allowing the generator 20 to power multiple instruments 2. Connector 58 is configured to couple to a bipolar instrument (not shown). When using the generator 20 in monopolar mode (e.g., with instruments 2), the return electrode 6 is coupled to the connector 54, which is associated with the screens 42 and 44. The generator 20 is configured to output the modes discussed above through the connectors 50, 56, 58.

Figure 3:
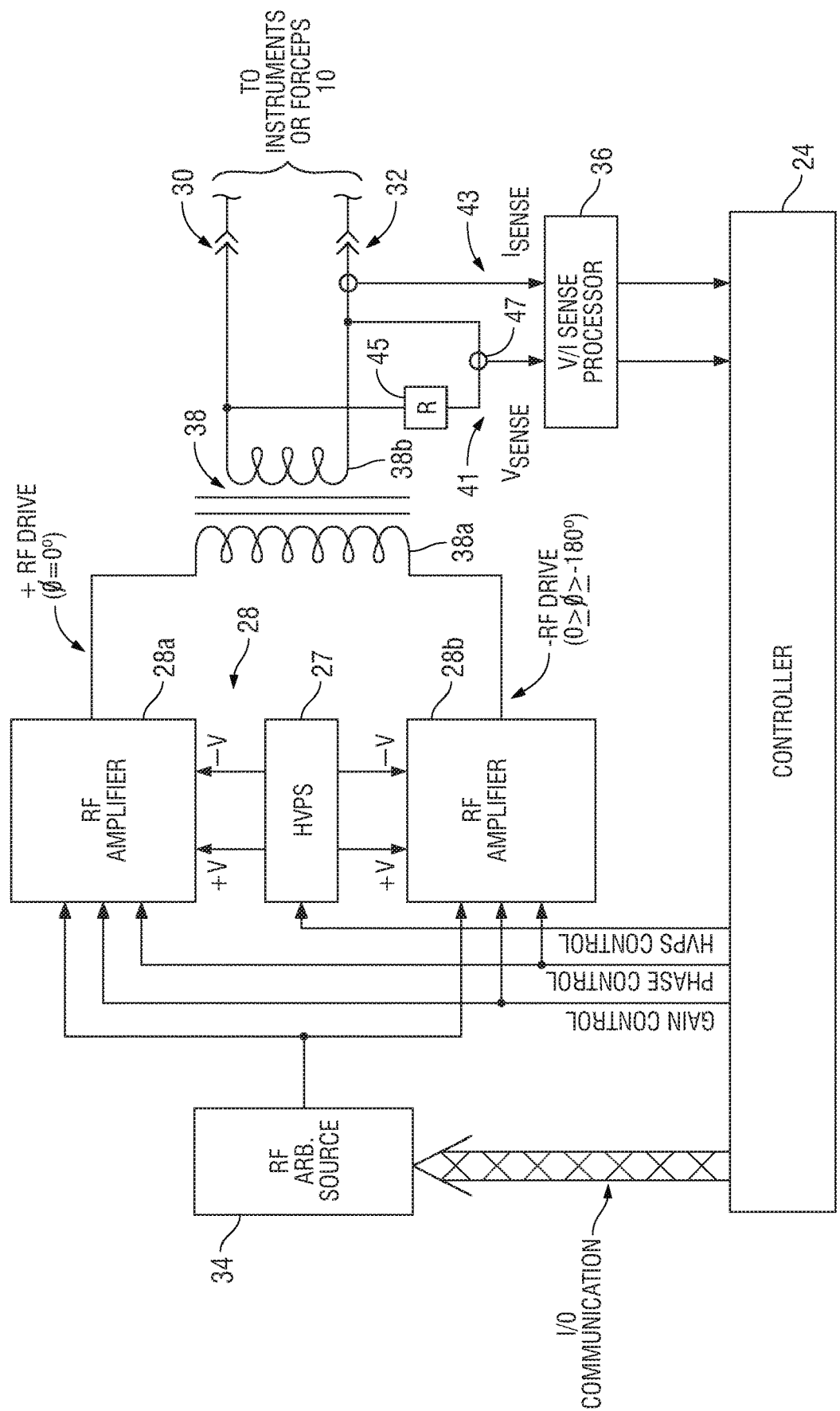
FIG. 3 is a schematic block diagram of the electrosurgical generator of FIG. 2 according to an embodiment of the present disclosure.

FIG. 3 shows a system block diagram of the generator 20 configured to output electrosurgical energy. The generator 20, a controller 24, a high voltage DC power supply 27 ("HVPS"), a radio frequency amplifier 28, including an RF amplifier 28a and an RF amplifier 28b, includes a radio frequency (RF) arbitrary source 34, a sense processor 36, and a patient isolation transformer 38 including a primary winding 38a and a secondary winding 38b.

The HVPS 27 of FIG. 3 is configured to output high DC voltage from about 15 V DC to about 200 V DC and is connected to an AC source (e.g., electrical wall outlet) and provides high voltage DC power to the RF amplifier 28, which then converts high voltage DC power into radio frequency energy and delivers the energy to the terminals 30 and 32, which are, in turn, coupled to the connectors 50-62 for supplying energy to the instrument 2 and the return pad 6 or the forceps 10. The HVPS 27 is coupled to the RF amplifiers 28a and 28b and provides DC energy thereto in a transparent manner to the operation of the RF amplifiers 28a and 28b. In particular, the controller 24 provides an HVPS control signal to drive the positive and negative potentials of the HVPS 27 for each of the RF amplifiers 28a and 28b with sufficient power to allow for uninhibited operation of the RF amplifiers 28a and 28b. In other words, the controller 24 may control the RF amplifiers 28a and 28b via the RF arbitrary source 34 or directly without adjusting the HVPS 27.

The RF arbitrary source 34 may be any RF signal generator such as a voltage controlled oscillator, a direct digital synthesizer, or any suitable frequency generator configured to generate arbitrary waveforms from a fixed frequency reference clock. As herein, the term "arbitrary" denotes an RF signal that may be any arbitrarily defined waveform, e.g., any frequency, amplitude, duty cycle, etc. The RF arbitrary source 34 supplies an RF signal to the RF amplifiers 28a and 28b. In embodiments, the RF signal may be a bipolar two-quadrant sinusoidal arbitrary RF signal. The RF amplifiers 28a and 28b process the RF arbitrary source signal and generate a differential RF drive signal to the patient isolation transformer 38. RF output parameters, such as operating RF power, voltage and current amplitude, operating frequency, gain parameters, phase compensation, time dependent configuration of the RF arbitrary source 34, are processed by the RF amplifiers 28a and 28b to deliver prescribed RF clinical treatment energy to achieve a desired tissue effect.

The RF amplifier 28a and RF amplifier 28b are coupled to the primary winding 38a of the patient isolation transformer 38. The RF amplifier 28a is configured to output a positive half-cycle having a phase angle from about 0° to about 180° and the RF amplifier 28b is configured to output a negative half-cycle having a phase angle from about 0° to about −180°. Thus, while the RF amplifier 28a is providing sourcing RF current (e.g., outputs positive current), the RF amplifier 28b is providing sinking current (e.g., outputs negative current). Conversely, while the RF amplifier 28b is providing sourcing RF current (e.g., outputs positive current), the RF amplifier 28a is providing sinking current (e.g., outputs negative current).

The patient isolation transformer 38 combines the differential RF drive output of the RF amplifiers 28a and 28b to deliver phase correlated RF energy (e.g., waveform) across to the secondary winding 38b to the terminals 30 and 32 with high signal-to-noise immunity to common-mode generated, spurious processing noise. In other words, the differential RF drive output provides the common mode rejection and cancels spurious corruptive noise energy from altering the prescribed clinical treatment tissue effect. This allows for the phase-correlated RF energy to be adjustable, providing potential for new control modes to dynamically alter in real-time the crest factor and other parameters of the delivered RF waveshape within a given applied energy activation period.

The sense processor 36 is coupled to a voltage sensor 41 and a current sensor 43. The voltage sensor 41 includes a resistor element 45 that provides an RF current weighted measurement of the delivered RF voltage to the terminals 30 and 32. A current transformer 47 then converts the weighted value of the RF voltage to provide a voltage sense signal to the sense processor 36 for processing. The current sensor 43 similarly provides a current sense signal to the sense processor 36.

The sense processor 36 then transmits the voltage and current sense signals to the controller 24, which adjusts RF output parameters in response to algorithm controls within a given RF activation period in real-time. In particular, the controller 24 adjusts the amplitude, frequency, waveshape and time-dependent configuration of the RF arbitrary source 34 during the given RF activation period to deliver a variety of RF treatment modes. The treatment modes may include waveforms having a duty cycle from about 5% to about 100% and may be either continuous waves or variant duty cycle RF bursts, or alternate in single or multiple combinations between modes to create a specific RF mode sequence. In embodiments, the controller 24 is configured to control the RF arbitrary source 34, the RF amplifier 28a and 28b, and/or the HVPS 27 in response to a selected electrosurgical operational mode, which may be selected from a plurality of electrosurgical operational modes. Each electrosurgical operational mode may be associated with at least one radio frequency input signal corresponding to a desired output electrosurgical waveform.

The controller 24 may include a microprocessor operably connected to a memory, which may be volatile type memory (e.g., RAM) and/or non-volatile type memory (e.g., flash media, disk media, etc.). The controller 24 may also include a plurality of output ports that are operably connected to the HVPS 27 and the RF amplifiers 28a and 28b allowing the controller 24 to control the output of the generator 20. More specifically, the controller 24 adjusts the operation of the HVPS 27 and the RF amplifiers 28a and 28b in response to a control algorithm that is implemented to track output of the RF amplifiers 28a and 28b to provide for sufficient power from the HVPS 27. In particular, as discussed in more detail below with respect to FIG. 4, the controller 24 supplies gain and phase control signals to each of the RF amplifiers 28a and 29b. In embodiments, a control algorithm may also inhibit or limit the output of RF amplifiers 28a and 28b to fit within the power supply limitations.

Figure 4:
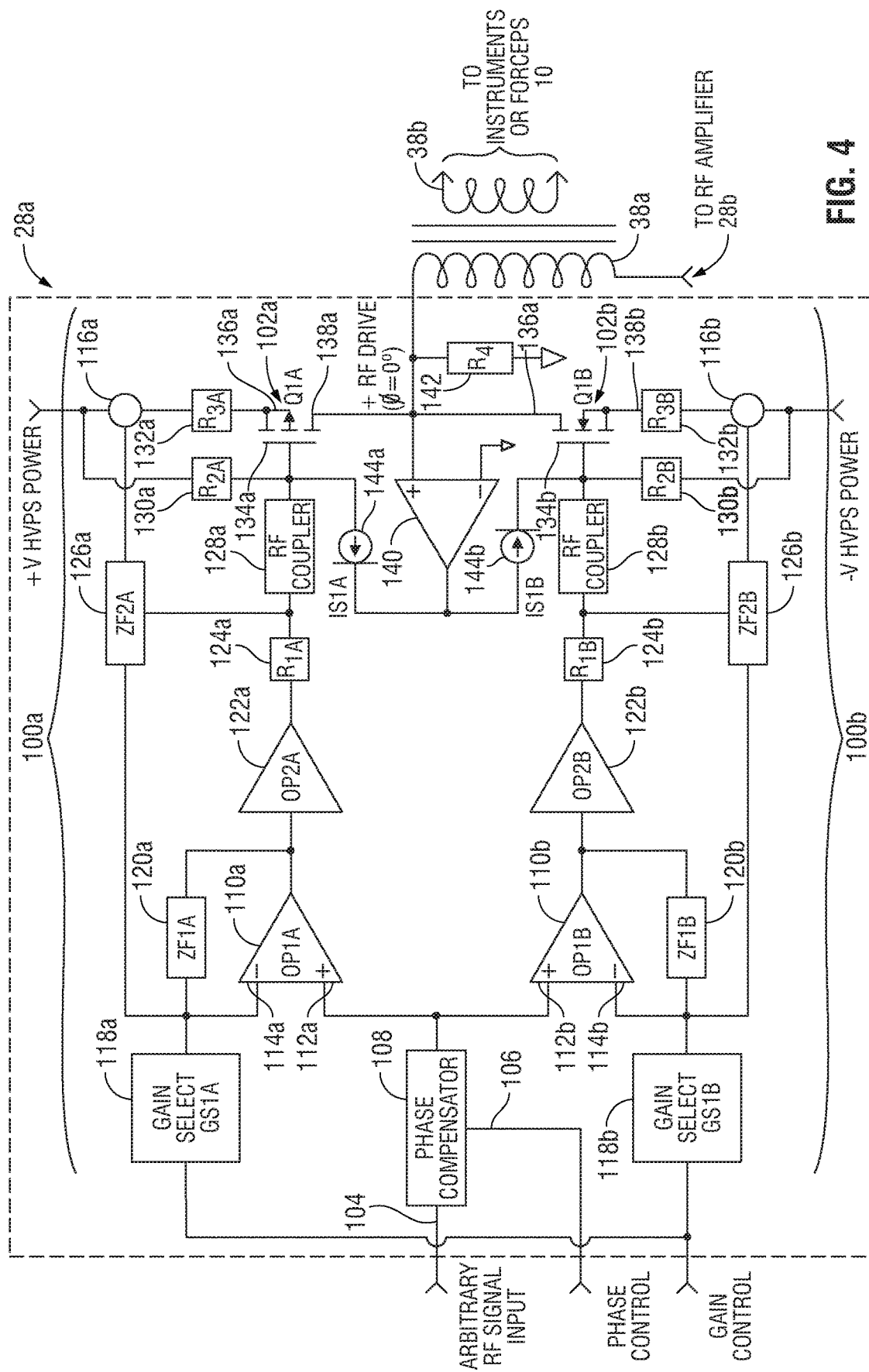
FIG. 4 is a schematic block diagram of a radio frequency amplifier of the electrosurgical generator of FIG. 3 according to an embodiment of the present disclosure.

FIG. 4 illustrates the components of the RF amplifier 28a. The circuit design of RF amplifier 28b is substantially similar to the RF amplifier 28a, with the exception for the phase relationship, as discussed above, accordingly, only the RF amplifier 28a is discussed. The RF amplifier 28a is a non-resonant multi-frequency transconductance amplifier configured to generate an RF current output for an applied RF voltage input. The RF voltage input signal may have an arbitrary waveshape as provided by the RF arbitrary source 34 as discussed above.

The RF amplifier 28a is configured to operate with two RF control loops 100a and 100b to control each of the components of an electrosurgical waveform, e.g., each half of an applied two-quadrant sinusoidal or non-sinusoidal arbitrary RF signal input, having symmetric or non-symmetric waveshape and variable timing, to address user configurable operating modes for achieving the desired clinical effect. RF control loops 100a and 100b are closed loop controlled RF channels where each positive or negative half of the applied sinusoidal input is processed independently. Control loop 100a processes the negative half-cycle of the applied sinusoidal input, driving a power component 102a to create a positive half cycle source current at the primary side 38a of the patient isolation transformer 38. Control loop 100b processes the positive half-cycle of the applied sinusoidal input, driving a power component 102b to create a negative half cycle source current at the primary side 38a of the patient isolation transformer 38. The power components 102a and 102b are shown as p-type and n-type metal-oxide semiconductor field-effect transistors, respectively. In embodiments, the power components 102a and 102b may be any p-type or n-type transistor, MOSFET, insulated gate bipolar transistor, (IGBT), relay, and the like. The patient isolation transformer 38 combines the developed RF current from the RF amplifiers 28a and 28b at the secondary winding 38b to generate the arbitrary sinusoidal RF output that is the supplied to the terminals 30 and 32 for delivery to the tissue site.

Only the control loop 100a is discussed in detail, since the control loop 100b is substantially identical with like components being labeled with same identifiers having a letter "b." The arbitrary RF signal from the RF arbitrary source 34 is applied at an input 104 of a phase compensator 108. In addition, a phase control signal from the controller 24 is applied at an input 106 at the phase compensator 108. The phase compensator 108 establishes the output phase of the RF amplifier 28a, which may be set to the desired phase (e.g., 0°) reference relative to the applied arbitrary RF signal input 104 in response to the phase control signal from the controller 24.

The phase compensator 108 provides a reference signal to an error correction amplifier 110a (or error correction amplifier 110b) at a positive input 112a. The error correction amplifier 110a is configured as an RF error correction amplifier that utilizes the reference signal at the positive input 112a to control the output current, which is sensed by an RF current sensor 116a and supplied to a negative input 114a of the error correction amplifier 110a. The error correction amplifier 110a outputs an RF control signal as a function of the reference signal and the detected output current. The RF current sensor 116a may be a current transformer, which may be a component of the current sensor 43. The RF current sensor 116a monitors the developed RF output current by converting the RF current to a signal voltage, which is then returned to the negative input 114a of the error correction amplifier 110a. A second frequency compensation network 126a provides frequency stability feedback compensation to the developed RF output current.

The first loop 100a also includes a gain selector 118a that provides a gain control adjustment to the output current control signal based on the gain controls signal supplied by the controller 24. The gain selector 118a is connected to the negative input 114a of the error correction amplifier 110a and provides gain modification to the RF current sensor 116a. The gain selector 118a is coupled to a first frequency compensating network 120a, which is used by the error correction amplifier 110a to map the output current to the applied reference voltage from the phase compensator 108. The frequency compensating network 120a provides stability corrected at the applied fundamental operating frequency of the arbitrary RF signal input to the sensed return signal detected by the RF current sensor 116a.

The error-corrected output signal of the error correction amplifier 110a is supplied to a gain amplifier 122a, which is configured as an RF gain cell to provide a forward path gain for the error correction output signal. The output of the gain amplifier 122a then drives the gate of the power component 102a through a resistor element 124a and RF coupler components 128a as the drive signal is elevated to the operating voltage of the HVPS 27. RF coupler components 128a may include, but are not limited to, a capacitor, a transformer, an optical coupler, combinations thereof, and the like. The gain amplifier 122a also drives a second frequency compensating network 126a to provide a second level of frequency compensation for the developed RF output current.

The power component 102a is shown as a MOSFET device having a gate contact 134a, a source contact 136a and a drain contact 138a. The power component 102a presents a transconductance gain, converting the drive voltage from the gain amplifier 122a to an RF output current, which is applied to the primary winding 38a. The power component 102a is coupled to a resistor element 130a at the gate contact 134a and a resistor element 132a at the +V HVPS power. The resistor element 130a establishes the DC bias operating level of the power component 102a and the resistor element 132a provides source degeneration to the developed current of the power component 102a.

The RF amplifier 28a also includes a stabilization amplifier 140, which is configured as a DC stabilization amplifier for monitoring the output DC voltage level generated by the output DC bias currents of the power components 102a and 102b flowing into a shunted resistor element 142. The DC voltage through the resistor element 142 is maintained at approximately 0 V DC by introducing steering error correction currents 144a and 144b via the stabilization amplifier 140 to the resistor elements 130a and 130b, respectively.

The stabilization amplifier 140 also provides a DC bias set point that establishes a relative transconductance gain match between power components 102a (e.g., p-channel MOSFET) and power component 102b (n-channel MOSFET), such that the positive and negative output peak currents delivered to the patient isolation transformer are symmetrically balances over the minimum and maximum dynamic range of the output current signal level.

Conventional electrosurgical generators have a slower response time in delivery of RF energy to the tissue, which results in less than optimal tissue effect. In particular, the response is slowed by the high voltage power supply, which controls the rate of change with which RF energy can be delivered to the tissue site. In such designs, a controller initially drives the high voltage power source, which then drives the RF output stage.

Further, conventional generators are based on various resonant output topologies. Resonant RF energy source operate at a unique switching frequency, which delivers both a fundamental RF operating frequency as well as additional switching frequency harmonics. The harmonic frequency components deliver an uncontrolled corruptive level of energy to the tissue, which may result in undesirable tissue effects. The harmonic frequency components also increase the RF high frequency leakage present in energy delivered to the patient.

Resonant-based RF generators also include reactive LC (inductor/capacitor) components to establish resonant operation. The LC components act as energy storage components due to resonant switching operation and may also discharge the stored energy into the tissue, thereby also resulting in undesirable tissue effects.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator comprising:
   a phase compensator configured to generate a reference signal based on a radio frequency signal and a phase control signal;
   at least one error correction amplifier coupled to the phase compensator, the at least one error correction amplifier configured to output a control signal based on the reference signal;
   a first radio frequency amplifier configured to generate a first component of at least one electrosurgical waveform based on the control signal and the phase control signal;
   a second radio frequency amplifier configured to generate a second component of the at least one electrosurgical waveform based on the control signal and the phase control signal; and
   a patient isolation transformer coupled to the first radio frequency amplifier and the second radio frequency amplifier, wherein the first and second components of the at least one electrosurgical waveform are combined at the patient isolation transformer to generate the at least one electrosurgical waveform.

2. The electrosurgical generator according to claim 1, further comprising:
   a gain selector configured to provide a gain control adjustment to the control signal based on a gain control signal.

3. The electrosurgical generator according to claim 2, further comprising:
   at least one gain amplifier coupled to the at least one error correction amplifier and the gain selector, the at least one gain amplifier configured to adjust the control signal based on the gain control adjustment.

4. The electrosurgical generator according to claim 1, further comprising:
   at least one current sensor coupled to at least one of the first radio frequency amplifier or the second radio frequency amplifier, the at least one current sensor configured to provide a signal representative of the at least one electrosurgical waveform to the at least one error correction amplifier.

5. The electrosurgical generator according to claim 4, further comprising:
   at least one frequency compensation network coupled to the at least one current sensor.

6. The electrosurgical generator according to claim 1, further comprising:
   at least one stabilization amplifier coupled to at least one of the first radio frequency amplifier or the second radio frequency amplifier, the at least one stabilization amplifier configured to introduce an error correction current into the at least one electrosurgical waveform based on DC bias current flowing from the at least one of the first radio frequency amplifier or the second radio frequency amplifier.

7. The electrosurgical generator according to claim 1, further comprising:
   a user input for selecting at least one electrosurgical operational mode; and
   a controller configured to adjust at least one of the radio frequency signal or the phase control signal in response to the at least one electrosurgical operational mode.

8. An electrosurgical generator comprising:
- a phase compensator configured to generate a reference signal based on a radio frequency signal and a phase control signal;
- at least one error correction amplifier coupled to the phase compensator, the at least one error correction amplifier configured to output a first control signal and a second control signal based on the reference signal;
- a first radio frequency amplifier configured to generate a first component of at least one electrosurgical waveform based on the first control signal and the phase control signal;
- a second radio frequency amplifier configured to generate a second component of at least one electrosurgical waveform based on the second control signal and the phase control signal; and
- a patient isolation transformer coupled to the first radio frequency amplifier and the second radio frequency amplifier, wherein the first and second components of the at least one electrosurgical waveform are combined at the patient isolation transformer to generate the at least one electrosurgical waveform;
- a user input for selecting at least one electrosurgical operational mode; and
- a controller configured to adjust at least one of the radio frequency signal or the phase control signal in response to the at least one electrosurgical operational mode.

9. The electrosurgical generator according to claim 8, further comprising:
- a first gain selector configured to provide a first gain control adjustment to the first control signal based on a first gain control signal provided by the controller; and
- a second gain selector configured to provide a second gain control adjustment to the second control signal based on a second gain control signal provided by the controller.

10. The electrosurgical generator according to claim 9, wherein the at least one error correction amplifier includes a first error correction amplifier and a second error correction amplifier, wherein further comprising:
- the first error correction amplifier is coupled to the phase compensator and configured to output the first control signal based on the reference signal; and
- the second error correction amplifier is coupled to the phase compensator and configured to output the second control signal based on the reference signal.

11. The electrosurgical generator according to claim 10, further comprising:
- a first gain amplifier coupled to the first error correction amplifier and the first gain selector, the first gain amplifier configured to adjust the first control signal based on the first gain control adjustment; and
- a second gain amplifier coupled to the second error correction amplifier and the second gain selector, the second gain amplifier configured to adjust the second control signal based on the second gain control adjustment.

12. The electrosurgical generator according to claim 11, further comprising:
- a first current sensor coupled to the first radio frequency amplifier, the first current sensor configured to provide a signal representative of the first component of the at least one electrosurgical waveform to the first error correction amplifier; and
- a second current sensor coupled to the second radio frequency amplifier, the second current sensor configured to provide a signal representative of the second component of the at least one electrosurgical waveform to the second error correction amplifier.

13. The electrosurgical generator according to claim 12, further comprising:
- a first frequency compensation network coupled to the first current sensor; and
- a second frequency compensation network coupled to the second current sensor.

* * * * *